(12) United States Patent
Lustgarten

(10) Patent No.: US 9,241,881 B2
(45) Date of Patent: *Jan. 26, 2016

(54) DENTAL MATERIAL AND METHOD

(71) Applicant: Stewart J. Lustgarten, Bellingham, MA (US)

(72) Inventor: Stewart J. Lustgarten, Bellingham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/211,958

(22) Filed: Mar. 14, 2014

(65) Prior Publication Data

US 2014/0271496 A1 Sep. 18, 2014

Related U.S. Application Data

(60) Provisional application No. 61/792,914, filed on Mar. 15, 2013.

(51) Int. Cl.
*A61K 6/087* (2006.01)

(52) U.S. Cl.
CPC ...................................... *A61K 6/087* (2013.01)

(58) Field of Classification Search
USPC .................................. 424/435, 484; 433/215
See application file for complete search history.

(56) References Cited

U.S. PATENT DOCUMENTS

| | | | | |
|---|---|---|---|---|
| 4,302,376 A | * | 11/1981 | Walkowiak et al. ... | A61K 6/083 106/35 |
| 4,624,256 A | * | 11/1986 | Messier et al. ......... | A61L 17/145 606/230 |
| 5,403,188 A | * | 4/1995 | Oxman et al. ................. | 433/218 |
| 6,013,122 A | * | 1/2000 | Klitzman et al. ........... | 106/31.03 |
| 6,290,982 B1 | * | 9/2001 | Seppala et al. ......... | A61K 6/033 424/426 |
| 6,530,958 B1 | * | 3/2003 | Cima et al. ................. | 623/23.51 |
| 7,858,141 B2 | * | 12/2010 | Getman et al. ......... | A01N 25/34 106/2 |
| 2011/0129801 A1 | * | 6/2011 | Barman ....................... | 433/215 |
| 2011/0182995 A1 | * | 7/2011 | Asgary ......................... | 424/489 |

OTHER PUBLICATIONS

Darwis, D. et al. (1998). "Heat Resistance of Radiation Crosslinked Poly(e-caprolactone)." Journal of Applied Polymer Science, 68: 581-588.*
Lachke, A. (2004) "Xanthan—A Versitile Gum." Resonance, 25-33.*
Darwis et al. (1998). Heat Resistance to Radiation Crosslinked Poly(e-caprolactone). Journal of Advanced Polymer Science, 68: 581-588.*
Darwis et al. (1998). Heat Resistance to Radiation Crosslinked Poly(e-caprolactone). Jounral of Advanced Polymer Science, 68: 581-588.*
Stephenson et al. (1961). Ultraviolet Irradiation of Plastics. II. Crosslinking and Scission. Journal of Polymer Science, 55: 465-475.*
Valles et al. (1990). Gelatioon of a radiation crosslinked model polyethylene. Rheological Acta, 29: 535-542.*
Lange (1986). Determination of the degree of swelling and crosslinking of extremely small polymer gel quantities by analytical ultracentrifugation. Colloid & Polymer Science, 264: 488-493.*

* cited by examiner

*Primary Examiner* — Frederick Krass
*Assistant Examiner* — Amanda Heyes

(57) ABSTRACT

A dental material composed of hydrophilic polycaprolactone formed by the process of exposing a hydrophobic caprolactone to ionizing irradiation from a radiation source selected from the group consisting of an Electron Acceleration (E beam), Gamma II, Cobolt, X-ray or a source of UV radiation to form a cross linked polycaprolactone composition consisting of two distinct phases one of which is soluble and the other non-soluble, and adjusting the duration of ionizing radiation and/or the intensity of the radiation to cause the concentration of the soluble phase to be above at least about 65% by weight of the cured polymeric composition whereby the hydrophobic caprolactone becomes hydrophilic.

13 Claims, No Drawings

DENTAL MATERIAL AND METHOD

This application claims the benefit of U.S. Provisional Application Ser. No. 61/792,914 filed on Mar. 15, 2013.

FIELD OF INVENTION

This invention is directed to a dental material and method of forming a dental material and more particularly to a dental material composed of hydrophilic polycaprolactone and method of forming hydrophilic polycaprolactone ("PCL") for use in restoring teeth, preparing a denture base material and for preparing pulpal liners and dental cements for all types of crown & bridge restorative procedures in dentistry.

BACKGROUND OF INVENTION

The etiology of teeth in a human's oral cavity are derived from the juxtaopposed denticle scales of a Shark's integument. Unlike, the overlapping fibrous collagen scales of the shark, higher orders and species of vertebrate fish, the human denticle scale, includes a slightly angulated vertical rearward projection from the scales surface. This projection allows for a supply of blood by means of a pulpal canal in the form of a soft calcium hydroxyappretite/collagen, covered over with a very hard calcium hydroxyapatite shell with, a rod-like/matrix structure, of enamel.

In modern day dentistry, even till this day, gold (Au) alone is the material of choice for restoring all non-aesthetic surfaces particularly where no mastication occurs on the direct biting and chewing surfaces of the teeth. Gold has many attributes in the restoration of these biting and chewing surfaces in that gold is relatively soft and malleable to cause stress breaks during traumatic opposing forces of mastication so as not to insult the periodontium and osteoclasts of the tooth and bone, respectively. The margins of a Class II restoration which has either necrotic decayed tissue removed on either proximal sides of the tooth and that of the occlusal surface at the interfacial Enamel/cavo surface margins where a gold inlay meets the enamel or in a gold cast crown where the entire margin is prepared circumferentially, the gingival margin may easily be burnished with an instrument making gold the material of choice for restoring surfaces at the margin.

The reason natural enamel on a human tooth surface protects the tooth surface and the reason a restored tooth surface using gold protects the tooth surface is that natural enamel and gold are hydrophilic materials. The hydrophilic property of the material provides for little, if any, surface tension, and causes hydrogen bonding, which inhibits the formation of a contact angle with water or saliva on its substrate surface thereby forming a boundary layer which permits frictionless laminar flow of saliva and/or food to flow over wear susceptible tooth masticatory surfaces which are otherwise areas susceptible to decay all around the tooth such is in a posterior tooth, in grooves and fossae or in the proximal embrasure areas of the teeth and between teeth. The hydrophilic surface on the teeth or tooth is nature's way of preventing decaying masticatory food from otherwise collecting, i.e., the decaying food will be carried away by the saliva.

However, today's modern dental materials currently conventionally used for restoring teeth are hydrophobic. A hydrophobic material causes high surface tension thereby inhibiting hydrogen bonding. Moreover, the hydrophobic nature of the material prevents the formation of a boundary layer and instead forms a turbulent surface which does not permit the saliva to flow over the tooth surface.

The dental composition of the subject invention is hydrophilic and has a very low surface energy which promotes hydrogen bonding. Moreover, because it is hydrophilic a boundary layer is formed having a small contact angle-free boundary layer when in contact with water or saliva. The boundary layer forms over the tooth substrate surface exactly as is formed with an enamel surface or a gold surface and provides for friction-less laminar flow of saliva in combination with particles of food, over these chewing surfaces which enhances their wear in the same manner as currently occurs with natural teeth or on gold surfaces.

SUMMARY OF THE INVENTION

The dental material of the present invention is composed of hydrophilic polycaprolactone formed by exposing a hydrophobic polycaprolactone monomer to ionizing irradiation from a radiation source selected from the group consisting of an Electron Acceleration (E beam), Gamma II, Cobolt, X-ray or a source of UV radiation sufficient to cross link the polycaprolactone monomer into a fully cured composition, which is substantially solid at room temperature, and consists of two distinct phases one of which is soluble and the other non-soluble, and varying the duration of ionizing radiation and/or the intensity of the radiation such that the soluble phase is above at least about 65% by weight of the cured composition for converting the hydrophobic caprolactone into a hydrophilic polycaprolactone.

DETAILED DESCRIPTION OF THE INVENTION

Applicant has discovered that hydrophobic caprolactone ("PCL") can be converted into a hydrophilic polycaprolactone ("PCL") for use in the restoration of teeth' or for preparing a denture base material and for preparing pulpal liners and dental cements for all types of crown & bridge restorative procedures in dentistry by cross linking a hydrophobic e Caprolactone monomer or an un-cross linked polycaprolactone having a molecular weight, between 25,000 and 75,000 and a melting point above 60° C. wherein the caprolactone is subjected to ionizing irradiation until cross linked into a solid polymer consisting of two distinct phases one of which is soluble and the other non-soluble and varying the duration of ionizing radiation and/or the intensity of the radiation until the soluble phase is above at least about 65% by weight of the cured composition and preferably above 68% by weight for converting the hydrophobic caprolactone into hydrophilic polycaprolactone.

It is known from the prior art, as is taught in U.S. Pat. No. 5,977,203, that one can cross link a caprolactone ("PCL") monomer by subjecting the caprolactone monomer to different forms of ionizing irradiation including gamma ray from cobalt 60 and/or electron beam radiation from an accelerator. The radiation cures the caprolactone monomer into a polymeric polycaprolactone indicative of the degree of crosslinking with the polymeric polycaprolactone consisting of a soluble component and an insoluble component in the form of a gel fraction. However, in accordance with the present invention it has been discovered that when the soluble component is above at least about 65% by weight of the polymeric polycaprolactone composition the polymeric polycaprolactone is converted into a hydrophilic material. This percentage is controlled by the duration of exposure, the type of radiation and/or the extent of radiation.

The hydrophilicity of the polycaprolactone composition is visually apparent by spreading a liquid such as water over the surface to see if the water spreads without the formation of droplets. The polycaprolactone composition can become an ideal hydrophilic material forming an extremely low contact angle with water of below 10° or near zero by solubilizing the composition with a solvent such as methyl ethyl ketone ("MEK"), ethyl acetate, tetrahydrafuran, or tricloromethane and filtering out the non-soluble component. This is taught in the corresponding application of applicant provisional application No. 61/793,189 filed on Mar. 15, 2013, for forming a material for use as a coating material composition for forming the exterior surface of a vessel to improve hydrodynamics. The corresponding application which claims priority to provisional application No. 61/793,189 filed on Mar. 15, 2013 is incorporated herein by reference. The irradiated PCL may be combined with a preferred solvent such as MEK and heated to above the melting temperature of the cross-linked "PCL" to cause the soluble phase to solubilize in the solvent forming a solute and with the insoluble phase remaining as an insoluble, gel-like mass which may readily be filtered away. Upon evaporation of the MEK solvent out in an evaporator under a fume hood exhaust, the remaining soluble phase solidifies and will exhibit "ideal" hydrophilic properties. The insoluble phase, is useful for other dental applications in that it exhibits a much higher melting temperature with far less shrinkage that that of "PCL", alone. Stated otherwise once the solute volatiles away and the cross linked ("XL-PCL") gel-like phase is completely dry and returns to a solid moldable thermoplastic polymer, which itself has a very high melting temperature but is not hydrophilic.

In the alternative and by reference to the concurrently filed application the cross-linking can also be accomplished using an already polymerized "PCL", in whatever form by subjecting the polymerized "PCL" to ionizing radiation as identified above provided the soluble phase is >65% and preferably above 68% by weight of the entire composition whereby the material composition becomes hydrophilic surface and can be used for the molding of denture teeth or other dental applications to inhibit wear.

In accordance with the subject invention the polymerized "PCL" composition Containing both the soluble and insoluble phases can be used for all of the dental applications as long as the soluble phase is present above at least 65% by weight of the entire composition or the soluble phase can be solubilized in a solvent and the insoluble phase filtered out.

Accordingly, the hydrophilic PCL polymer composition of this invention can be used either in solubilized form or as a solid for the fabrication of Crowns, Bridges and Inlays and Denture and Partial Denture base materials and also for their polymeric posterior, false teeth. The above compositions can also be for thermoplastic polymer moldable material for the moldable fabrication of Dental Crowns, Bridges, Posterior Denture Teeth and Pink Denture Base Material where hydrophilicty is a desirable denture retention property for the tissue bearing surface of the Denture, by either molding the denture base material from the Thermoplastic hydrophilic material of this invention in a conventional manner or by coating its tissue bearing surface of denture base materials.

Example I

The following composition allows for a hydrophilic surface to be formed over the chewing surfaces of teeth and restores the back surfaces of the teeth to their near original integrity using hydrophilic polycaprolactone referred to hereinafter as composition A formed by the process of exposure to radiation as taught hereinabove. This composition also contains 2 parts of a non-leachable electrophoretic, anti-microbial surface throughout, even if abraded using a vinyl silane coupling agent to couple the Ammonium chloride finely divided particle as described in U.S. Pat. No. 7,858,141, the disclosure of which is herein incorporated by reference. The composition also contains barium sulfate which is radio opaque so that when the composition is inserted within a tooth restoration and the tooth is restored it provides an outline of where the internal restoration is proximal to the natural dentin and also contrasts it with any possible re-current decay that may have taken place in those internal proximal areas. The preferred composition of this example includes by weight:

Composition I

A. 83 parts—of hydrophilic polycaprolactone (composition A)
B. 15 parts—Barium sulfate (X-Ray Radio-opacity)
C. 02 parts—Antimicrobial Agent.

Example II

Heat Part A from the above composition I to its melting temperature of 165 F degrees+/−2 degress. Incorporate parts B & C in a suitable vessel which is then placed in water at 170 F. degrees and stir admixture using an appropriate stirring method until all the admixture is of uniform color and consistency and then remove vessel from hot water and allow to cool.

Alternatively, place Part-A of composition I into a preferred diluent such as Methyl Ethyl Ketone (MEK) in a suitable vessel and heat with hot water to 130-175 degrees, Then add Part B and C in the vessel and store in an evaporator with fume hood until all MEK has volatized, away. When this method is employed in its manufacture, equal parts of Poyynyl actetate and/or Polyvinyl alcohol, or combinations of both may be added to promote adhesion and which also forms a boundary layer but only after a delay of some minutes and where the composition forms a boundary layer on a tooth surface with saliva within only one (1) minute.

Example III

A (For: Crowns, Bridges and, Pontics

A. 97 parts of Part "A" from composition I in Example I
B. 03 parts of an Antimicrobial Agent such as Part "C" of composition I, above.

B "For Denture Base Material"

A. 94% of Part "A"
B. 0 to 3 parts of Antimicrobial Agent Part "C" of composition I, above.
C. 0 to 3 Parts of 1 part, Red, 1+ or −, 1 part, White+ or − and 1 part, Yellow+ or minus, to a suitable gum of either inorganic pigment or organic pigment.

C For Dental Polymer Cement

A. 7-8 Parts of Part "A" from composition I
B. 2 parts Polyvinyl Acetate (Cas No. 9003-20-7)
C. 2 parts Polyvinyl Alcohol (Cas No. 9002-89-5)
D. 79-81 parts Ethyl Acetate, Diluent and Vehicle (Cas No. 144-78-6)
E. 0.40 parts, Fumed Colloidal Silica (Cab-o-Sil) (CAS No. 112945-52-2) and remainder F. up to 8 Parts—Calcium hydroxide (Cas No. 1305-62-0)

Method of Manufacture Pulpal Axial Wall Bonding Agent & Liner for Cavity Preparations and Crowns Preferred Composition A. 05.54 of Part "A" above from example I
B. 04.00 parts Polyvinyl Acetate
C. 02.00 parts Polyvinyl Alcohol
D. 10 parts Calcium hydroxide
E. 78.46 Parts, Ethyl Acetate

What is claimed is:

1. A dental material having a hydrophilic surface comprising a cross linked caprolactone polymeric material and barium sulfate with the dental material formed by the process comprising exposing a hydrophobic caprolactone monomer or hydrophobic polycaprolactone to a source of ionizing irradiation selected from the group consisting of an Electron Acceleration (E beam), Gamma II, Cobolt, X-ray or a source of UV radiation until the unirradiated hydrophobic caprolactone or unirradiated hydrophobic polycaprolactone is cross linked into a solid polycaprolactone polymeric material consisting of a soluble component part and an insoluble component part with the insoluble component part being in the form of a gel fraction % of soluble to insoluble parts, adjusting the duration of ionizing radiation and/or the intensity of the radiation until the concentration of the soluble component part in percentage part is above at least about 65% by weight of the total polycaprolactone polymeric material and with the irradiated the polycaprolactone polymeric material possessing a hydrophilic surface, heating the polycaprolactone polymeric material at a temperature up to its melting temperature and incorporating barium sulfate to form the dental material.

2. A dental material as defined in claim 1 wherein said barium sulfate is in a concentration of at least about 10% by weight of the dental material.

3. A dental material as defined in claim 1 further comprising at least about 0.02 parts of an antimicrobial agent comprising a silicon containing quaternary ammonium salt.

4. A method of forming a dental material having a hydrophilic surface for use in treating or restoring one or more teeth of a dental patient comprising the steps of selecting a material comprising a hydrophobic caprolactone monomer or hydrophobic polycaprolactone, subjecting the selected material to a source of ionizing irradiation selected from the group consisting of an Electron Acceleration (E beam), Gamma II, Cobolt, X-ray or a source of UV radiation to cross link the hydrophobic caprolactone monomer or hydrophobic polycaprolactone into a solid cross linked polycaprolactone polymeric material consisting of a soluble component part and an insoluble component part in a gel fraction % of soluble to insoluble parts; with the insoluble part in the form of a gel, adjusting the duration of ionizing radiation and/or the intensity of the radiation until the concentration of the soluble component part in percentage is above at least about 65% by weight of the total cross linked polycaprolactone polymeric material and with the polycaprolactone polymeric material possessing a hydrophilic surface, heating the irradiated polycaprolactone polymeric material into a softened state at a temperature up to its melting temperature to form said dental material and applying said dental material in said softened state to a surface of a tooth or teeth in the preparation of a dental restoration.

5. A method as defined in claim 4 further comprising the steps of incorporating an antimicrobial agent and/or a radio opaque additive of barium sulfate into said polycaprolactone polymeric material after being heated up to its melting temperature.

6. A method as defined in claim 4 wherein said dental material comprises at least about 83 parts of said polycaprolactone polymeric material.

7. A method as defined in claim 5 wherein said solid cross linked polycaprolactone polymeric material is diluted in methyl ethyl ketone before being heated in a suitable vessel in water at a temperature of between 130 to 175° F. and before either said antimicrobial agent and/or said radio opaque additive is added thereto.

8. A method as defined in claim 7 wherein said antimicrobial agent comprises a silicon containing quaternary ammonium salt.

9. A method as defined in claim 4 using at least 97 parts of said hydrophilic polycaprolactone dental material for forming a dental crown or bridge.

10. A method of forming a polycaprolactone polymeric material having a hydrophilic surface for use as a dental material in the preparation of a dental cement, dental bonding agent or dental liner comprising the steps of subjecting a hydrophobic caprolactone monomer or hydrophobic polycaprolactone to a source of ionizing irradiation selected from the group consisting of an Electron Acceleration (E beam), Gamma II, Cobolt, X-ray or a source of UV radiation to form a solid cross linked polycaprolactone polymeric material consisting of a soluble component part and an insoluble component part in a gel fraction % of soluble to insoluble parts, adjusting the duration of ionizing radiation and/or the intensity of the radiation until the concentration of the soluble component part is above at least about 65% by weight of the total cross linked polycaprolactone polymeric material and with the polycaprolactone polymeric material possessing a hydrophilic surface heating the polycaprolactone polymeric material into a softened state at a temperature up to its melting temperature and adding polyvinyl acetate, polyvinyl alcohol and ethyl acetate to formulate a dental cement, dental bonding agent or dental liner.

11. A method as defined in claim 10 wherein said-hydrophilic polycaprolactone dental material further comprises fumed colloidal silica and calcium hydroxide.

12. A method as defined in claim 10 for use in forming a dental liner wherein said hydrophilic polycaprolactone dental material further comprises ethyl acetate, polyvinyl acetate, polyvinyl alcohol and calcium hydroxide.

13. A method as defined in claim 7 further comprising filtering out part or all of the insoluble component part of the polycaprolactone polymeric material after the polycaprolactone polymeric material is heated wherein the remaining polycaprolactone polymeric material is hydrophilic and is composed substantially or entirely of the soluble component part.

* * * * *